United States Patent
Ebanks et al.

(10) Patent No.: US 12,318,469 B2
(45) Date of Patent: Jun. 3, 2025

(54) COSMETIC COMPOSITIONS CAPABLE OF FORMING A MULTILAYER STRUCTURE AFTER APPLICATION TO A KERATINOUS MATERIAL CONTAINING A COMBINATION OF SILICONE RESINS

(71) Applicant: L'ORÉAL, Paris (FR)

(72) Inventors: Jody Ebanks, Clark, NJ (US); Hubert Tunchiao Lam, Berkeley Heights, NJ (US); Tsang-Min Huang, Scotch Plains, NJ (US); Frances San George, Springfield, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 16/916,594

(22) Filed: Jun. 30, 2020

(65) Prior Publication Data
US 2021/0401723 A1    Dec. 30, 2021

(51) Int. Cl.
| | | |
|---|---|---|
| A61K 8/891 | (2006.01) | |
| A61K 8/92  | (2006.01) | |
| A61Q 1/04  | (2006.01) | |
| A61Q 1/10  | (2006.01) | |
| A61Q 5/06  | (2006.01) | |

(52) U.S. Cl.
CPC ............... *A61K 8/891* (2013.01); *A61K 8/92* (2013.01); *A61Q 1/04* (2013.01); *A61Q 1/10* (2013.01); *A61Q 5/065* (2013.01)

(58) Field of Classification Search
None
See application file for complete search history.

(56) References Cited

U.S. PATENT DOCUMENTS

| | | |
|---|---|---|
| 2,230,063 A | 1/1941 | Klimist et al. |
| 3,787,337 A | 1/1974 | Goodwin |
| 4,683,134 A | 7/1987 | Palinczar |
| 4,699,779 A | 10/1987 | Palinczar |
| 4,767,741 A | 8/1988 | Komor et al. |
| 4,795,631 A | 1/1989 | Sheehan |
| 4,797,273 A | 1/1989 | Linn et al. |
| 5,641,493 A | 6/1997 | Date et al. |
| 5,665,368 A | 9/1997 | Lentini et al. |
| 5,674,508 A | 10/1997 | Deserable |
| 5,747,001 A | 5/1998 | Wiedmann |
| 5,747,013 A | 5/1998 | Mougin et al. |
| 5,849,834 A | 12/1998 | Matsuzaki et al. |
| 5,882,635 A | 3/1999 | Ramin et al. |
| 5,985,297 A | 11/1999 | Mellul et al. |
| 6,001,374 A | 12/1999 | Nichols |
| 6,019,962 A | 2/2000 | Rabe et al. |
| 6,039,960 A | 3/2000 | Chung et al. |
| 6,071,503 A | 6/2000 | Drechsler et al. |
| 6,340,466 B1 | 1/2002 | Drechsler et al. |
| 6,362,353 B1 | 3/2002 | Ellis |
| 6,387,405 B1 | 5/2002 | Shah et al. |
| 6,406,683 B1 | 6/2002 | Drechsler et al. |
| 6,482,398 B1 | 11/2002 | Rabe et al. |
| 6,620,417 B1 | 9/2003 | Jose et al. |
| 6,811,770 B2 | 11/2004 | Ferrari et al. |
| 7,785,574 B2 | 8/2010 | Bobka et al. |
| 9,205,039 B2 | 12/2015 | Brown et al. |
| 10,675,226 B2 | 6/2020 | El-Khouri |
| 2001/0031268 A1 | 10/2001 | Baldwin et al. |
| 2002/0015683 A1 | 2/2002 | Nichols et al. |
| 2002/0022009 A1 | 2/2002 | Poterie et al. |
| 2002/0127192 A1 | 9/2002 | Murphy |
| 2003/0077962 A1 | 4/2003 | Krzysik et al. |
| 2004/0081633 A1 | 4/2004 | Mercier et al. |
| 2004/0141933 A1 | 7/2004 | Luo et al. |
| 2004/0197284 A1 | 10/2004 | Auguste |
| 2005/0008667 A1 | 1/2005 | Liechty et al. |
| 2005/0089498 A1 | 4/2005 | Patil et al. |
| 2005/0186166 A1 | 8/2005 | Patil et al. |
| 2005/0201961 A1 | 9/2005 | Lu et al. |
| 2005/0226832 A1 | 10/2005 | Bobka et al. |
| 2005/0238979 A1 | 10/2005 | Dumousseaux |
| 2005/0244355 A1 | 11/2005 | Sabino et al. |
| 2005/0244442 A1 | 11/2005 | Sabino et al. |
| 2005/0249758 A1 | 11/2005 | Di Puccio Pagano |
| 2005/0276763 A1 | 12/2005 | Pfeifer et al. |
| 2006/0013789 A1 | 1/2006 | Blin et al. |
| 2006/0088483 A1 | 4/2006 | Thevenet |
| 2006/0275226 A1 | 12/2006 | Dahms |
| 2006/0292096 A1 | 12/2006 | Yu |
| 2007/0093619 A1 | 4/2007 | Bui et al. |

(Continued)

FOREIGN PATENT DOCUMENTS

| | | |
|---|---|---|
| DE | 31 12943 A1 | 10/1982 |
| DE | 698 32 545 T2 | 9/2006 |
| EP | 0 336 902 A2 | 10/1989 |
| EP | 0 795 318 A2 | 9/1997 |
| EP | 0 823 250 A2 | 2/1998 |
| EP | 1 051 968 A2 | 11/2000 |
| EP | 1 192 937 A2 | 4/2002 |
| EP | 1 604 635 A2 | 12/2005 |
| EP | 1 604 644 A | 12/2005 |
| EP | 1 913 929 A2 | 4/2008 |
| EP | 2 116 221 A1 | 11/2009 |
| EP | 2 599 472 B1 | 11/2016 |

(Continued)

OTHER PUBLICATIONS

International Search Report and Written Opinion Issued Oct. 21, 2021 in PCT/US2021/038628, 16 pages.

(Continued)

*Primary Examiner* — David J Blanchard
*Assistant Examiner* — Edwin Coleman Mitchell
(74) *Attorney, Agent, or Firm* — Womble Bond Dickinson (US) LLP

(57) ABSTRACT

Cosmetic compositions capable of forming a multilayer structure after application to a keratinous material containing a combination of silicone resins are provided, as well as methods of applying such compositions to a keratinous material.

13 Claims, No Drawings

(56) References Cited

U.S. PATENT DOCUMENTS

| | | | |
|---|---|---|---|
| 2007/0104667 | A1 | 5/2007 | Mondet |
| 2007/0166271 | A1 | 7/2007 | Gordon et al. |
| 2008/0305056 | A1 | 12/2008 | Jenni et al. |
| 2008/0305068 | A1 | 12/2008 | Zheng et al. |
| 2009/0098068 | A1 | 4/2009 | Takakura |
| 2009/0317344 | A1 | 12/2009 | Zhang |
| 2011/0038820 | A1 | 2/2011 | Barba et al. |
| 2011/0147259 | A1 | 6/2011 | Binder et al. |
| 2012/0308500 | A1 | 12/2012 | Hart |
| 2013/0045913 | A1 | 2/2013 | Germaneau et al. |
| 2013/0046029 | A1 | 2/2013 | Germaneau et al. |
| 2013/0164229 | A1 | 6/2013 | Mendoza |
| 2014/0154196 | A1 | 6/2014 | Cavazzuti et al. |
| 2014/0154199 | A1 | 6/2014 | Dussaud et al. |
| 2015/0366779 | A1 | 12/2015 | Bui et al. |
| 2015/0366782 | A1 | 12/2015 | Bui et al. |
| 2016/0000691 | A1 | 1/2016 | Mohammadi et al. |
| 2017/0135946 | A1 | 5/2017 | Novack et al. |
| 2017/0281478 | A1* | 10/2017 | El-Khouri ............... A61K 8/03 |
| 2017/0281518 | A1 | 10/2017 | El-Khouri |
| 2017/0281519 | A1 | 10/2017 | El-Khouri |
| 2017/0281520 | A1 | 10/2017 | El-Khouri |
| 2017/0281521 | A1 | 10/2017 | El-Khouri |
| 2018/0000721 | A1* | 1/2018 | SaNogueira ............. A61K 8/35 |
| 2018/0116947 | A1 | 5/2018 | Scotland et al. |
| 2018/0177712 | A1* | 6/2018 | El-Khouri ............... A61K 8/89 |

FOREIGN PATENT DOCUMENTS

| | | |
|---|---|---|
| FR | 2 771 628 A1 | 6/1999 |
| FR | 2 771 629 A | 6/1999 |
| FR | 2 918 272 A1 | 1/2009 |
| FR | 2 921 266 B1 | 6/2012 |
| FR | 2 978 037 B1 | 1/2014 |
| GB | 795841 | 5/1958 |
| JP | H10-067624 | 3/1998 |
| JP | 2000-219617 A | 8/2000 |
| JP | 2015-520118 | 7/2015 |
| WO | WO 96/36310 A1 | 11/1996 |
| WO | WO 2005/046626 A2 | 5/2005 |
| WO | WO 2005/075567 A1 | 8/2005 |
| WO | WO 2007/026101 A1 | 3/2007 |
| WO | WO 2009/006218 A2 | 1/2009 |
| WO | WO 2009/080953 A2 | 7/2009 |
| WO | WO 2009/080958 A2 | 7/2009 |
| WO | WO 2009/105294 A2 | 8/2009 |
| WO | WO 2011/100275 A1 | 8/2011 |
| WO | WO 2012/038879 A2 | 3/2012 |
| WO | WO 2012/064714 A2 | 5/2012 |
| WO | WO 2013/088051 A2 | 6/2013 |
| WO | WO 2013/102727 A1 | 7/2013 |
| WO | 2014095821 | 6/2014 |
| WO | 2015193413 A1 | 12/2015 |
| WO | 2017173267 | 3/2017 |
| WO | 2017173270 | 3/2017 |
| WO | WO 2018/062725 A1 | 4/2018 |
| WO | WO 2019/022437 A1 | 1/2019 |

OTHER PUBLICATIONS

"Xiameter® PMX-200 Silicone Fluid 30,000 CS," Xiameter® Material Safety Data Sheet, Version 3.0, published Sep. 13, 2017, p. 1-12.
"Xiameter® PMX-200 Silicone Fluid, 5,000-60,000 est," Xiameter® from Dow Corning, published Feb. 18, 2015, p. 1-3.
"Mega Last Liquid Lipstick Liquid Lipstick: Improved Color Intensity, Non-transfer," Formulation 01451, Dow Corning, Formulation Information Color Cosmetics©, 2010 Dow Corning Corporation, p. 1-2.
Alex C.M. Kuo, "Poly(dimethylsiloxane)," Polymer Data Handbook©, 1999 by Oxford University Press, Inc., p. 1-25.
International Search Report and Written Opinion issued Jul. 11, 2017 In PCT/US 2017/025376.
"Triethoxy Caprylylsilane Treatment-11S," Kobo Products Inc., published Jul. 14, 2017.
"Introduction to Silicone Fluids," Clearco Products Co., Inc.,p. 1-4, Aug. 7, 2006.
French Preliminary Search Report issued May 17, 2021 in Patent Application No. FR 2008714 (with English translation of categories of cited documents), 14 pages.
"Amplifiant Volume and Definition Effect Lipstick" Database GNPD [Online] MINTEL, XP055804860, Apr. 20, 2018, 4 pages.
"Top of the Line Eyeliner Pencil" Database GNPD [Online] MINTEL, XP055804868, Apr. 1, 2021, 3 pages.
Susan C. Smolinske "Handbook of Food, Drug, and Cosmetic Excipients" CRC Press LLC, 1992, p. 231 (with cover pages).
"Glossy Full Couleur Extreme Shine Lip Gloss", Make Up For Ever, Product No. 1522027, Mar. 2011, 3 pages.
Marie Contier et al., "Characterization of the tack and gloss of cosmetic formulations", LVMH Recherche Parfums & Cosmetiques Materials Innovation Department, May 13, 2016, pp. 1-5 (with English translation).
Written Opinion issued Jul. 21, 2008, in French Patent Application No. 0854940.
"Basic Properties of PARLEAM®", NOF Corporation Oleo & Specialty Chemicals Div., Apr. 2015, 2 pages.
"Report on tests carried out by the company L'Oréal in response to the notice of opposition formed by the company Parfums Christian Dior against patent EP 2 618 803 B1", L'Oréal, Jun. 19, 2017, pp. 1-3 (with English translation).
"ETHOCEL", Ethylcellulose Polymers Technical Handbook, Dow Cellulosics, Sep. 2005, pp. 1-28.
Charles M. Hansen, "The Three Dimensional Solubility Parameter—Key to Paint Component Affinities: I. Solvents, Plasticizers, Polymers, and Resins", Journal of Paint Technology, vol. 39, No. 505, Feb. 1967, pp. 104-117.
Notice of Opposition issued Jan. 6, 2017 in European Patent Application No. 2 618 803 B1 (with English translation).
Response to Notice of Opposition issued Jun. 19, 2017 in European Patent Application No. 2 618 803 (with English translation).
Oct. 21, 2015, Notice of Opposition issued in European Application No. 2 618 811.
Nov. 4, 2015 Office Action issued in U.S. Appl. No. 13/824,533.
Mar. 11, 2016 Office Action issued in U.S. Appl. No. 13/824,548.
Mar. 31, 2016 Office Action issued in U.S. Appl. No. 14/370,335.
Oct. 8, 2015 Office Action issued in U.S. Appl. No. 14/370,335.
EWG, "Polysorbate-60", printed 2019.
Chemical Book, Mineral Oil, pp. 1-2 (Nov. 20, 2018) (Year:2018).
"Colour Gloss Extension", MINTEL No. 10116327, Aug. 2002, 2 pages.
Mclain, "Final Report of the Cosmetic Ingredient Review Expert Panel on the Safety Assessment of Polyisobutene and Hydrogenated Polyisobutene as Used in Cosmetics", International Journal of Toxicology, 27 (Suppl. 4) pp. 83-106, 2008.
Melzer et al., "Ethylcellulose: a new type of emulsion stabilizer," European Journal of Pharaceutics and Biopharmaceuticals, 56:23-27, 2003.
Wikipedia, "Talk:polybutene" 2012; https://en.wikipedia.org/wiki/Talk%3APolyubutene.
"Smooth Cover Gel," Database GNPD [Online] Mintel, Sep. 2009, XP-002658176, pp. 1-2.
"Mousse Foundation Natural Bronzing Effect," Database GNPD [Online] Mintel, Nov. 2010, XP-002658177, pp. 1-2.
"Ceramide Moisture Network Night Cream [Ingredients]," Database GNPD [Online] Mintel, Sep. 2004, XP-002658178, pp. 1-2.
"Beauty Body Gel," Database GNPD [Online] Mintel, Sep. 2010, XP-002658179, pp. 1-2.
"Butter Shine Lipstick," Database GNPD [Online] Mintel, Oct. 2008, XP-002658180, pp. 1-2.
"Lip Polish," Database GNPD [Online] Mintel, Jun. 2010, XP-002658181.
"Liquid Foundation," Database GNPD [Online] Mintel, Sep. 2010, XP-002658182.
May 6, 2011 French Search Report and Written Opinion issued in French Patent Application No. FR 1057526 (with translation).

(56) References Cited

OTHER PUBLICATIONS

May 6, 2011 French Search Report and Written Opinion issued in French Patent Application No. FR 1057528 (with translation).
Sep. 5, 2011 French Search Report and Written Opinion issued in French Patent Application No. FR 1060600 (with translation).
Sep. 5, 2011 French Search Report and Written Opinion issued in French Patent Application No. FR 1060650 (with translation).
Sep. 5, 2011 French Search Report and Written Opinion issued in French Patent Application No. FR 1060652 (with translation).
Apr. 3, 2012 Written Opinion of the International Searching Authority issued in International Application No. PCT/182011/054087.
Mar. 26, 2013 International Preliminary Report on Patentability issued in International Application No. PCT/IB2011/054087.
Apr. 3, 2012 International Search Report issued in International Application No. PCT/IB2011 /054087.
International Search Report issued in International Patent Application No. PCT/EP2011/066208 dated Mar. 29, 2012.
International Preliminary Report on Patentability issued in International Patent Application No. PCT/EP2011/066208 dated Mar. 26, 2013.
Mar. 10, 2014 Office Action issued in U.S. Appl. No. 13/824,548.
Feb. 13, 2014 Office Action issued in U.S. Appl. No. 13/824,548.
Oct. 31, 2012 French Search Report and Written Opinion issued in French Patent Application 1250017 (with English Translation).
Dec. 24, 2014 Office Action issued in Japanese Application No. 2013-528824. (with English Translation).
Flirt-Tinis Protective Lip Balm, XP-002731953, Sep. 2008, pp. 1-3.
Makingcosmetics.com article "Making emulsions for cosmetics," dated Oct. 12, 2004.
Google date for makingcosmetics.com article printed 2014.
Wikipedia, Hydrocarbon, (accessed Feb. 26, 2015) pp. 1-5.
Wikipedia, Triethanolamine, (accessed Feb. 26, 2015) pp. 1-6.
SAAPedia, Octyldodecyl stearoyl stearate (Oct. 28, 2014) pp. 1-2.
Love to Know Makeup (Jun. 11, 2008), pp. 1-4 (Year: 2008).
Chemical Land, Dihydroxyacetone accessed Jun. 6, 2019, pp. 1-2 (Year:2019).
European Food Safety Authority, Mineral Oil Hydrocarbon, (Jun. 6, 2012) pp. 1-2 (Year:2012).
10, 2015 Office Action issued in Chinese Application No. 201180055831.3.
Why balsam and vanishing cream in the cosmetics are classified as "water-in-oil" type and a "oil-in-water" type?, 2015.
Arbonne product "Lip Polish", Technical document.
Tendertones SPF 12 (Purring), XP-002731954, Aug. 2007, pp. 1-2.
Lip Moisture Cream SPF 30, XP-002731955, Apr. 2006, pp. 1-3.
Nov. 13, 2014 Search Report and Written Opinion issued in French Application No. 1452985.
Nov. 14, 2013 Office Action issued in Korean Application No. 10-2013-7018815.
Nov. 28, 2013 Office Action issued in Korean Application No. 10-2013-7021162.
"Making Emulsions for Cosmetics," makingcosmetics.com, Oct. 12, 2004.
Google search results for "cosmetic and emulsion," Nov. 30, 2014.
Mar. 11, 2015 Office Action issued in U.S. Appl. No. 13/824,533.
Dec. 18, 2014 Office Action issued in U.S. Appl. No. 13/824,548.
"Colour Gloss Extension", Clarins, Product No. 10116327, Aug. 2002.
Sagitani, "Making Homogeneous and Fine Droplet O/W Emulsions Using Nonionic Surfactants", JAOCS, pp. 738-743, 1981.
Chinese Office Action dated Mar. 8, 2024 (with English translation), from related CN Application No. 202180039300.9, filed Jun. 23, 2021; 10 pages.
Office Action issued Sep. 6, 2024, in Chinese Application No. 202180039300.9, with English translation.
Office Action issued Sep. 12, 2023, in Japanese Application No. 2022-566695, with English translation.
Notice of Allowance issued May 13, 2024, in Japanese Application No. 2022-566695, with English translation.

\* cited by examiner

COSMETIC COMPOSITIONS CAPABLE OF FORMING A MULTILAYER STRUCTURE AFTER APPLICATION TO A KERATINOUS MATERIAL CONTAINING A COMBINATION OF SILICONE RESINS

FIELD OF THE INVENTION

The present invention relates to cosmetic compositions capable of forming a multilayer structure after application to a keratinous material containing a combination of silicone resins. Such compositions allow for benefits associated with multilayer cosmetic products without having to engage in a multi-step application process.

DISCUSSION OF THE BACKGROUND

Many cosmetic compositions, including pigmented cosmetics such as foundations, lipsticks and eye shadows, have been formulated in an attempt to possess long wearing properties upon application. Unfortunately, many of these compositions do not generally possess both good long-wear/transfer-resistance properties as well as good application properties, good comfort properties and/or good appearance properties (for example, shine, or matte properties).

For example, with respect to lip products, commercial products containing silicon resins such as MQ resins are known. Such products are known to provide good long wear properties and/or transfer-resistance. However, such products possess poor application properties, poor feel upon application (for example, feel rough) and poor shine or gloss properties owing to the film formed by the MQ resin (for example, a matte appearance). Therefore, a second composition (topcoat) is separately applied to such products to improve poor properties of the compositions to make the products acceptable to consumers. Furthermore, the topcoat composition must be reapplied continually so that the product remains acceptable to consumers, meaning that the products are effectively not "long-wearing" as they require constant maintenance and reapplication.

With respect to foundations, such products can provide good long wear properties and/or transfer-resistance. However, such long-wearing/transfer-resistant products can possess poor application and/or feel upon properties application, as well as poor matte properties.

Thus, there remains a need for improved "single step" cosmetic compositions having improved cosmetic properties, particularly good wear, feel, radiance, luminosity, and/or matte characteristics upon application.

SUMMARY OF THE INVENTION

The present invention relates to anhydrous cosmetic compositions capable of forming a multilayer structure after application to a keratinous material, wherein the compositions comprise at least two immiscible components prior to application and wherein the compositions comprise at least one modified MQ resin, at least one MQ resin, and at least polypropylsilsesquioxane resin. Preferably, the compositions further comprise at least one colorant.

The present invention also relates to methods of treating, caring for and/or making up a keratinous material (for example, skin, hair, eyelashes, nails or lips) by applying compositions of the present invention to the keratinous material in an amount sufficient to treat, care for and/or make up the keratinous material.

The present invention also relates to methods of enhancing the appearance of a keratinous material (for example, skin, hair, eyelashes, nails or lips) by applying compositions of the present invention to the keratinous material in an amount sufficient to enhance the appearance of the keratinous material.

The present invention also relates to methods of applying compositions of the present invention to a keratinous material (for example, skin, hair, eyelashes, nails or lips) comprising mixing or blending the composition so that the immiscible components are temporarily miscible, and applying the composition comprising the temporarily miscible components to the keratinous material. Subsequent to application to the keratinous material, the components separate to form a multilayer structure on the keratinous material.

The present invention also relates to kits comprising (1) at least one container; (2) at least one applicator; and (3) at least one composition of the present invention. Preferably, the at least one container is configured to mix immiscible components in the at least one composition of the present invention.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number.

All amounts or percent concentrations expressed herein refer to amounts or percents based on weight with respect to the total weight of the composition.

"Immiscible" in the context of "immiscible component" as used herein means that the components are visually separated into layers in a composition, similar to a mixture of oil and vinegar in which the oil and vinegar form separate layers in a composition. By way of contrast, an emulsion containing an oil phase and a water phase does not contain immiscible oil and water components because the emulsion does not contain visually separated layers.

"Temporarily miscible" in the context of blending or mixing compositions such that immiscible components are "temporarily miscible" as used herein means that the components are not visually separated into layers after blending or mixing.

"Film former" or "film forming agent" as used herein means a polymer or resin that leaves a film on the substrate to which it is applied.

"Polymer" as used herein means a compound which is made up of at least two monomers.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2, 3, 4, 5, 6, 7, 8, 9, 10, 11, 12, 13, 14 or 15 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Adhesion" as used herein refers to the quality exhibited by compositions that adhere to a substrate after application. Adhesion may be evaluated by any method known in the art for evaluating such. For example, samples to be tested for adhesion properties can be deposited onto a surface such as a bioskin substrate or Byko-Charts Black Scrub Panels P122-10N (6.50×17.00 inches). After drying, a piece of ASTM cross hatch tape (Permacel 99/PA-28060/51596) can be placed on the sample, and removed at a 180° angle. Then, it can be determined how much of the sample is adhered to the tape. For example, a rating scale such as a scale of 1-3 can be used to assess the degree of sample removal from the substrate onto the tape, in which 1 is essentially no removal, 2 is some removal, and 3 is essentially complete removal.

The term "rub-off resistance" as used herein refers to physical abrasion such as rubbing the human skin with the hands or clothes or other physical interaction. It can also be described as the ability to hold active ingredients on the skin or prevent the removal of active ingredients from the skin or a substrate such as Byko-Charts Black Scrub Panels P122-10N (6.50×17.00 inches) or bioskin by abrasion or other physical interaction.

"Gloss" in compositions as used herein refers to compositions having with an average gloss, measured at 60°, of greater than or equal to 35, for example 40, preferably 45, 55, 60 or 65 out of 100, including all ranges and subranges therebetween such as 35-65, 40-65, etc.

The term "average gloss" denotes the gloss as it can be measured using a gloss meter, for example by spreading a layer of the composition to be tested via a 1 mL draw down, between 20 μm and 500 μm in thickness, on a black panel using an automatic spreader. The deposit can be left to dry for a definite time period such as 24 or 48 hours at a temperature of room temperature and then the gloss is measured at 60° using a Byk Gardner gloss meter of reference microTRi-GLOSS. This measurement (of between 0 and 100) is repeated at least three times, and the average gloss is the average of the at least three "Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to the skin and evaluating the color of the composition after an extended period of time. For example, the color of a composition may be evaluated immediately following application to skin and these characteristics may then be re-evaluated and compared after a certain amount of time. Further, these characteristics may be evaluated with respect to other compositions, such as commercially available compositions. Alternatively or additionally, long wear properties may be evaluated by applying a sample, allowing it to dry, and then abrading the sample to determine removal/loss of sample.

The cosmetic compositions and methods of the present invention can comprise, consist of, or consist essentially of the essential elements and limitations of the invention described herein, as well as any additional or optional ingredients, components, or limitations described herein or otherwise useful in personal care.

Compositions Capable of Forming a Multilayer Structure

In accordance with various embodiments of the present invention, cosmetic compositions capable of forming a multilayer structure after application to a keratinous material containing a combination of silicone resins are provided. Such compositions allow for benefits associated with multilayer cosmetic products without having to engage in a multi-step application process. For example, such compositions can be suitable as foundations, primers, eye shadows and other skin compositions and/or can be suitable as lipsticks, lip glosses, lip balms and other lip compositions.

In accordance with one or more embodiments of the present invention, the cosmetic compositions of the present invention comprise at least two Components, hereinafter referred to as "Component A" and "Component B." In one or more embodiments, both Component A and Component B comprise silicone. Component A, for example, may comprise a combination of silicone resins. Component B, for example, may comprise a silicone gum.

Component A is the component of the compositions of the present invention which forms the layer of the multilayer structure which is closest to the keratinous material after application of the composition to the keratinous material. This layer of the multilayer structure is hereinafter referred to as "Layer A." In accordance with preferred embodiments, Component A/Layer A has an affinity for the surface of the keratinous material owing to the surface energy characteristics between the two.

Component B is the component of the compositions of the present invention which forms the layer of the multilayer structure which is farthest away from the keratinous material after application of the composition to the keratinous material. This layer of the multilayer structure is hereinafter referred to as "Layer B." In accordance with preferred embodiments, Component B/Layer B has an affinity for the air interface.

In accordance with the present invention, all weight amounts and ratios set forth herein referring to Component A and Component B refer to amounts of active material (that is, non-volatile material) in these components. Similarly, all weight amounts and ratios set forth herein referring to Layer A and Layer B refer to amounts of active material as Layer A and Layer B are present after evaporation of volatile solvent.

Prior to application to a keratinous material, Component A and Component B are immiscible in the compositions of the present invention. Preferably, immiscibility of the immiscible components results from an incompatibility between the two components when the composition is at rest, incompatibility between the two components after application to a keratinous material, or both.

In one or more embodiments, immiscibility of the immiscible components results from differences such as, for example, differences in viscosity, glass transition temperature, interfacial tension, solubility parameters, density, and/or chemical/structural incompatibility of the components, and/or differences induced by temperature and/or pressure.

For example, immiscibility of the immiscible components when the composition is at rest can result from, for example, chemical/structural incompatibility, differences in the interfacial tension between the components such as, for example, differences in the interfacial tension between the phases within mutually compatible solvent(s), differences in viscosity, differences in the glass transition temperatures of the polymers within each phase and/or differences induced by temperature and/or pressure.

For example, immiscibility of the immiscible components when the composition is being applied can result from, for example, chemical/structural incompatibility, differences in the interfacial tension between the components, differences in density of the components after solvent evaporation, and/or differences induced by temperature and/or pressure.

In one or more embodiments, immediately prior to application and/or during application to a keratinous material, the composition of the present invention is mixed or blended such that Component A and Component B are temporarily miscible upon application of the composition of the present invention to a keratinous material.

After the composition of the present invention has been applied to a keratinous material, Component A separates from Component B. As the composition dries on the keratinous material to which it has been applied, immiscible Component A and Component B form a multilayer structure comprising Layer A and Layer B, respectively, on the keratinous material such as, for example:

| LAYER B |
| LAYER A |
| KERATINOUS MATERIAL |

According to one or more embodiments of the present invention, after compositions of the present invention have been applied to a keratinous material, Component B results in Layer B which is level: that is, Layer B is planar such that it may have refractive properties to impart shine to the composition. In accordance with these embodiments, Component B has self-leveling properties: it results in a level Layer B after application. The shine of such compositions can be enhanced, if desired, by addition of one or more shine or gloss enhancing agents having high refractive index properties. Alternatively, such compositions can be provided with matte properties by addition of one or more mattifying agents.

According to preferred embodiments of the present invention, after compositions of the present invention have been applied to a keratinous material, Component B results in Layer B which is not-level: that is, Layer B is not planar such that it imparts matte properties to the composition. In accordance with these embodiments, Component B does not have self-leveling properties: it results in a non-level Layer B after application. The matte properties of such compositions can be enhanced, if desired, by addition of one or more mattifying agents. Alternatively, such compositions can be provided with shine or luminosity or gloss properties by addition of one or more shine or luminosity or gloss enhancing agents having high refractive index properties. Another benefit of the compositions may be that, when used as a base layer/primer, the self-leveling nature of the compositions may provide a smoothing surface, thereby reducing the appearance of skin imperfections.

In accordance with the present invention, the multilayer structure comprises Layer A and Layer B. In certain instances, depending on factors such as ingredient ratios, ingredient concentrations, solvent evaporation characteristics, and Tg of polymers, the layers might be intermixed slightly with each other after application to a keratinous material, resulting in Layer A having a larger amount of A and a smaller amount of B greater and/or Layer B having a larger amount of B and a smaller amount of A. Preferably, Layer A comprises 40% or less of Layer B, preferably 30% or less of Layer B, preferably 20% or less of Layer B, preferably 10% or less of Layer B, and preferably 5% or less of Layer B, including all ranges and subranges therebetween. Similarly, preferably, Layer B comprises 40% or less of Layer A, preferably 30% or less of Layer A, preferably 20% or less of Layer A, preferably 10% or less of Layer B, and preferably 5% or less of Layer A, including all ranges and subranges therebetween.

Factors affecting the separation of Component A and Component B after application to a keratinous material can include, for example, those properties discussed above including but not limited to the surface energy of the substrate, the density of each Component, the evaporation properties of the solvent(s), the Tg of the film formers, and/or the viscosity of the film formers.

Although not wishing to be bound by any particular theory, it is believed that Component A has surface energy properties closer to the surface energy properties of the keratinous material to which it is applied than Component B. For example, the surface energy of skin is estimated to be 36 mN/m. Accordingly, where Component A has a surface energy of about 36 mN/m, it is believed that Component A can migrate to the skin. Component B would preferably have a lower surface energy, making it more likely that it would migrate toward the air interface.

Although not wishing to be bound by any particular theory, it is believed that interfacial tension of Components A and B affects phase separation (in particular, the rate at which the Components A and B separate after application). It is believed that such phase separation can be affected by differences such as those discussed above such as, for example, differences in temperature of the Components A and B, in the Tg of the Components A and B (the higher the Tg of a component, the longer it will take for phase separation), in the weight fraction of the film formers, and/or in the pressure of the Components A and B.

Such differences will also be discussed further below.

Glass Transition Temperature (Tg)

According to preferred embodiments, Component A and/or Component B comprises a combination of silicone resins having at least one glass transition temperature lower than 60° C., preferably lower than 55° C., preferably lower than 50° C., and preferably lower than normal human body temperature (98.6° F. or 37° C.).

A preferred method of determining Tg is to remove all volatile solvent from the Layer, and determine Tg by Differential Scanning calorimetry.

Density

According to preferred embodiments, Component A and Component B have different density properties, and the difference is such that Component A and Component B are immiscible in the compositions of the present invention. Preferably, Component A/Layer A and Component B/Layer B have a density difference of 0.001-1 kg/m$^3$, preferably 0.005-0.8 kg/m$^3$, and preferably 0.01-0.6 kg/m$^3$, including all ranges and subranges therebetween.

Temperature

According to preferred embodiments, Component A and Component B are affected by temperature, and the effect is such that Component A and Component B are immiscible in the compositions of the present invention at temperatures below 50° C. for a predetermined amount of time as is known in the art unlike emulsions which are considered to be stable under such conditions.

Weight Fraction

According to preferred embodiments, Component A and/or Component B comprises at least one polymer such as, for example a film-forming agent having a critical molecular weight of entanglement ($M_c$) such that:

If present in Component A, the at least one polymer has an $M_c$<wMw, where w=weight fraction and Mw=molecular weight of the polymer; and If present in Component B, the at least one polymer has $M_c \leq wMw \leq 10^8$ g/mol.

Further, according to preferred embodiments, the viscosity of the at least one polymer in Component B is greater than 350 cSt, preferably greater than 500 cSt, preferably greater than 750 cSt, and preferably greater than 1000 cSt, including all ranges and subranges therebetween.

Ingredients

Component A and Component B can differ in various ways based primarily on the different functionalities associated with Layer A and Layer B. For example, where Layer A performs a transfer-resistance or adherence function, ingredients of Component A can be chosen to effect transfer-resistance or adherence. Similarly, where Layer A performs a color-enhancing function, at least one coloring agent can be added to Component A. And, for example, where Layer B performs a gloss- or shine-enhancing function and/or and provides a better feel (for example, affords a more comfortable feeling) and/or provides a barrier layer to inhibit color transfer, ingredients of Component B can be chosen to effect gloss, shine, comfort and/or barrier layer properties. However, it should be understood that at the interface of Layer A and Layer B, the interface of Layer A may possess properties more associated with Layer B (for example, shine) while Layer B may possess properties more associated with Layer A (for example, adhesion).

According to preferred embodiments, Component A comprises a combination of silicone resins, and optionally at least one coloring agent, and Layer A provides adhesion, transfer-resistance and/or color properties to the multilayer structure. According to such embodiments, Component B may comprise at least one shine-enhancing agent, at least one comfort agent and/or at least one barrier agent, and Layer B provides shine, comfort and/or barrier properties to the multilayer structure.

According to preferred embodiments, the compositions of the present invention contain less than 1% fluorinated compound.

According to preferred embodiments, the compositions of the present invention contain less than 0.5% fluorinated compound.

According to preferred embodiments, the compositions of the present invention contain no fluorinated compound.

According to preferred embodiments, at least one of the same solvent(s) is used in Component A and Component B. Preferably, of total solvent present in each Component, the majority in each Component is the same.

According to preferred embodiments, the weight ratio of Component A to Component B is from, for example, 1:50 to 1.5:1, 1:75 to 1.5:1, 1:50 to 1.5:1, 1:20 to 1.5:1, 1:50 to 50:1, 1:75 to 20:1, 1:50 to 10:1, or 1:20 to 10:1, including all ranges and subranges therebetween Examples of acceptable ingredients added to Component A and/or Component B are discussed below.

Combination of Silicone Resins

According to the present invention, compositions comprising at least one modified MQ resin, at least one MQ resin, and at least one polypropylsilsesquioxane resin are provided.

As used herein, the term "resin" means a crosslinked or non-crosslinked three-dimensional structure. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares one oxygen when the unit is part of a polymer. The "M" unit can be represented by the following structure:

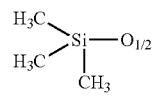

At least one of the methyl groups of the M unit may be replaced by another group, e.g., to give a unit with formula $[R(CH_3)_2]SiO_{1/2}$, as represented in the following structure:

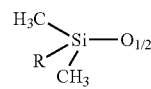

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

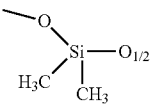

At least one of the methyl groups of the D unit may be replaced by another group, e.g., to give a unit with formula $[R(CH_3)]SiO_{2/2}$.

The symbol T denotes the trifunctional unit, $(CH_3)SiO_{3/2}$ and can be represented as:

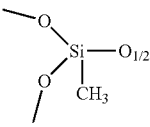

At least one of the methyl groups of the T unit may be replaced by another group, e.g., to give a unit with formula $[R]SiO_{3/2}$.

Finally, the letter Q means a tetrafunctional unit $SiO_{4/2}$ in which the silicon atom is bonded to four hydrogen atoms, which are themselves bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

MO resin, also known as trimethylsiloxysilicate, may be represented by the following formula:

$[(CH_3)_3SiO]_x(SiO_{4/2})_y$ (i.e., MQ units) wherein x and y may, for example, range from 10 to 150, preferably 20 to 120, preferably 40 to 100, and preferably 50 to 80.

Resin MQ, which is available from Wacker, Momentive Performance Materials, Grant Industries, Siltech, Milliken, and Dow Corning, is an example of an acceptable commercially-available trimethylsiloxysilicate. Further, trimethylsiloxysilicate is commercially available from Momentive Performance under the tradename SR1000 and from Wacker under the tradename TMS 803. MQ resin is also commercially available from Dow Chemical in a solvent, such as for example, cyclomethicone. However, according to the present invention, MQ resin may be used in the form of 100% active material, that is, not in a solvent.

Silsesquioxanes, on the other hand, may be represented by the following formula:

$(RSiO_{3/2})_x$ (i.e., T Units) wherein x may, for example, have a value of ranging from a few to up to several thousand.

Polypropylsilsesquioxanes are silsesquioxanes, in which R is a propyl group. These compounds and their synthesis are described, for example, in patent application WO 2005/075567, the entire contents of which is hereby incorporated by reference in its entirety.

Examples of commercially available polypropylsilsesquioxane resins that may be mentioned include those sold by the company Dow Corning under the reference Dow Corning 670 Fluid or 680 Fluid. Typically, such commercially available products are polypropylsilsesquioxane diluted in volatile oil such as volatile hydrocarbon oil or volatile silicone oil such as D5. Dow Corning 670 and 680 Fluids have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5,000, 7,000, 10,000, 15,000, 20,000, 25,000 to about 30,000, 50,000, 75,000, 100,000 g/mol and a Tg of less than about 37° C., from about −100, −50, −37, or −20 to about 37° C.

Preferably, the at least one MQ resin and the at least one polypropylsilsesquioxane resin are blended prior to addition to the compositions of the present invention. An example of such a commercial resin to polypropylsilsesquioxane in isododecane.

A modified MQ resin is an MQ resin in which at least one of the methyl groups of the M unit is replaced by another group described above. Preferably, the at least one M unit is replaced by a T unit. Suitable T units for such replacements include, but are not limited to, polysilsesquioxanes of formula $((R)SiO_{3/2})_x$ (T units) in which x is greater than 100, in which the R groups may independently be methyl or other substituents as defined above, polymethylsilsesquioxanes which are polysilsesquioxanes in which R is a methyl group, polypropylsilsesquioxanes in which R is a propyl group, and polyphenylsilsesquioxanes in which R is a phenyl group. Preferably, the MQ resin is modified with one or more polymethylsilsesquioxanes. An example of such a T-modified MQ resin is GRANRESIN MQI-150 from Grant Industries.

According to preferred embodiments, the weight ratio of (MQ resin+polypropylsilsesquioxane) to modified MQ resin is from about 10:1 to about 1:10, preferably about 5:1 to about 1:5, preferably about 3:1 to about 1:3, and preferably about 2:1 to about 1:2, including all ranges and subranges therebetween.

According to preferred embodiments, the amount of (MQ resin+polypropylsilsesquioxane) present in the compositions of the present invention ranges from about 5% to about 45%, preferably from about 7% to about 40%, and preferably from about 10% to about 35%, by weight with respect to the total weight of the composition, including all ranges and subranges therebetween.

According to preferred embodiments, the amount of MQ resin present in the compositions of the present invention ranges from about 2.5% to about 30%, preferably from about 3.5% to about 26%, and preferably from about 5% to about 22%, by weight with respect to the total weight of the composition, including all ranges and subranges therebetween.

According to preferred embodiments, the amount of polypropylsilsesquioxane present in the compositions of the present invention ranges from about 2.5% to about 15%, preferably from about 3.5% to about 14%, and preferably from about 5% to about 13%, by weight with respect to the total weight of the composition, including all ranges and subranges therebetween.

According to preferred embodiments, the amount of modified MQ resin present in the compositions of the present invention ranges from about 5% to about 45%, preferably from about 7% to about 40%, and preferably from about 10% to about 35%, by weight with respect to the total weight of the composition, including all ranges and subranges therebetween.

It is to be understood that the compositions of the present invention may optionally further comprise other film forming agents known in the art in addition to the combination of silicone resins described above. However, according to preferred embodiments, the compositions of the present invention do not contain any film forming agents other the combination of silicone resins discussed above. If other film forming agent(s) are present, the film forming agent(s) is/are preferably present in an amount of from about 0.05% to about 20% by weight, preferably from 0.1% to 15% by weight, and preferably from 0.5% to 10% by weight of the total weight of the component in which they are found, including all ranges and subranges therebetween.

Silicone Compounds

In one or more embodiments, compositions of the present invention comprise at least one silicone compound. Preferably, Component B comprises one or more silicone compounds which is not a film-forming agent. Also preferably, the at least one silicone compound has a surface energy lower than that of the film forming agent(s) in another component. So, for example, where Component B contains at least one silicone compound which is not a film-forming agent, the silicone compound preferably has a surface energy which is lower than that of film-forming agent(s) in Component A.

The silicone compound may be, for example, polymeric, comprising a silicon bonded to a minimum of one oxygen, and in even further embodiments, two oxygens. In some embodiments, the silicon is bonded to a hydrocarbon (e.g., C1-22 linear, branched, and/or aryl) such as methyl, ethyl, propyl, and phenyl. In one or more embodiments, the silicone compound comprises a polydimethylsiloxane (PDMS). In some embodiments, the silicone compound itself may be linear, branched or dendritic. In further embodiments, the silicone compound is linear or substantially linear. In one or more embodiments, the silicone compound comprises a chain termination selected from the group consisting of hydrocarbon, alcohol, ester, acid, ketone, amine, amide, epoxy, vinylogous (e.g. alkene or alkyne group), halogen, hydride, and the like. For example, in embodiments where the silicone compound comprises polydimethylsiloxane, the compound may be chain end terminated with an —OH or a methyl group.

In one or more embodiments, the term "silicone compound" includes, but is not limited to, silicone gums, silicone fluids, and silicone wax. If present, the silicone compound may impart properties on the composition (e.g., enhance shine or matte quality). In one or more embodiments, the silicone compounds are present in an amount sufficient to achieve a viscosity of greater than about 1,000 cSt and/or less than about 22,000,000 cSt. In some embodiments, the viscosity ranges from about 1,000, 5,000, 10,000, 20,000, 30,000, 40,000, 50,000 or 60,000 cSt to about 100,000, 200,000, 300,000, 400,000, 500,000, 600,000, 700,000, 800,000, 900,000, 1,000,000, 5,000,000, 10,000,000 or 22,000,000 cSt, including all ranges and subranges therebetween. A particularly preferred viscosity range for the combination of silicone compound(s) present in the compositions of the present invention is from 20,000 cSt to 800,000 cSt, with 25,000 cSt to 750,000 cSt being most preferred.

Shine/Luminosity Enhancing Agents

According to preferred embodiments of the present invention, at least one shine enhancing agent can be added to Component A, Component B, or both. Preferably, the shine enhancing agent is selected from the group consisting of agents which facilitate self-leveling of a layer, agents which have a high refractive index, and mixtures thereof. As described below, such shine enhancing agents may be silicone compounds discussed above.

In the case of compositions for skin, in particular foundation compositions, such shine enhancing agents may impart a luminous and/or dewy effect to compositions described herein. For example, one trend for foundation a dewy/radiant foundation (particularly long-lasting radiance), rather than a fully matte appearance. This is usually achieved through the addition of oils or pearls to the formula, but such formulas may not be long-lasting. The compositions described herein may result in both a dewy/radiant appearance that is also long-lasting.

Suitable shine enhancing agents include those compounds having a refractive index ranging from about 1.45 to about 1.60, and a weight average molecular weight of preferably less than 15,000, preferably less than 10,000, and preferably less than 2,000. Examples of such agents include, but are not limited to, phenylated silicones such as those commercialized under the trade name "ABIL AV 8853" by Goldschmidt, those commercialized under the trade names "DC 554", "DC 555", "DC 556" and "SF 558" by Dow Corning, and those commercialized under the trade name "SILBIONE 70633 V 30" by Rhone-Poulenc.

Additional examples of suitable phenylated silicones include, but are not limited to, those commercialized by Wacker Silicones such as BELSIL PDM 20, a phenylated silicone with a viscosity at 25° C. of approximately 20 cSt; BELSIL PDM 200, a phenylated silicone with a viscosity at 25° C. of approximately 200 cSt; BELSIL PDM 1000, a phenylated silicone with a viscosity at 25° C. of approximately 1000 cSt.

Additional examples of suitable shine enhancing agents include, but are not limited to, polycyclopentadiene, poly(propylene glycol) dibenzoate (nD=1.5345), aminopropyl phenyl trimethicone (nD=1.49-1.51) pentaerythrityl tetraoleate commercially available as PURESYN 4E68 (nD=1.473) from ExxonMobil, and PPG-3 benzyl ether myristate commercially available as CRODAMOL STS (nD=1.4696) from Croda Inc.

Particularly preferred shine enhancing agents are the phenylated silicones such as phenyl trimethicone, and trimethyl pentaphenyl trisiloxane, and esters such as pentaerythrityl tetraoleate, and PPG-3 benzyl ether myristate.

Suitable shine enhancing agents include those which provide self-leveling properties to the compositions of the present invention. Suitable examples of such compositions include, but are not limited to, the silicone gums discussed below.

The silicone gum can correspond to the formula:

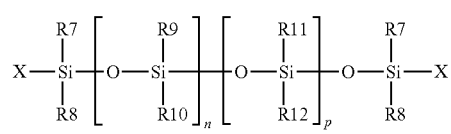

in which:
R$_7$, R$_8$, R$_{11}$ and R$_{12}$ are identical or different, and each is chosen from alkyl radicals comprising from 1 to 6 carbon atoms,
R$_9$ and R$_{10}$ are identical or different, and each is chosen from alkyl radicals comprising from 1 to 6 carbon atoms and aryl radicals,
X is chosen from alkyl radicals comprising from 1 to 6 carbon atoms, a hydroxyl radical and a vinyl radical,
n and p are chosen so as to give the silicone gum a viscosity of from 350 cSt to 50,000,000 cSt, preferably from 500 cSt to 40,000,000 cSt, preferably from 750 cSt to 30,000,000 cSt, preferably from 850 cSt to 20,000,000 cSt, preferably from 950 cSt to 18,000,000 cSt and preferably from 1000 cSt to 10,000,000 cSt, including all ranges and subranges therebetween.

In general, n and p can each take values ranging from 0 to 10,000, such as from 0 to 5,000.

Among the silicone gums which can be used according to the invention, mention may be made of those for which:
the substituents R$_7$ to R$_{12}$ and X represent a methyl group, p=0 and n=2 700, such as the product sold or made under the name SE30 by the company General Electric,
the substituents R$_7$ to R$_{12}$ and X represent a methyl group, p=0 and n=2 300, such as the product sold or made under the name AK 500 000 by the company Wacker,
the substituents R$_7$ to R$_{12}$ represent a methyl group, the substituent X represents a hydroxyl group, p=0 and n=2 700, as a 13% solution in cyclopentasiloxane, such as the product sold or made under the name Q2-1401 by the company Dow Corning,
the substituents R$_7$ to R$_{12}$ represent a methyl group, the substituent X represents a hydroxyl group, p=0 and n=2 700, as a 13% solution in polydimethylsiloxane, such as the product sold or made under the name Q2-1403 by the company Dow Corning, and
the substituents R$_7$, R$_8$, R$_{11}$, R$_{12}$ and X represent a methyl group and the substituents R$_9$ and R$_{10}$ represent an aryl group, such that the molecular weight of the gum is about 600 000, for instance the product sold or made under the name 761 by the company Rhone-Poulenc (Rhodia Chimie).

In preferred embodiments, the silicone gum correspond to the following formula:

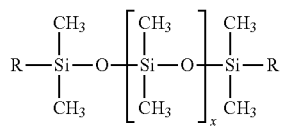

In this formula the terminal Si's can also be other than methyl and may be represented with substitutions on the repeating Si such that the R group is an alkyl of 1 to 6 carbon atoms, which may be linear, branched and/or functionalized selected from methyl, ethyl, propyl, isopropyl, butyl, isobutyl, t-butyl, amyl, hexyl, vinyl, allyl, cyclohexyl, phenyl, and mixtures thereof. The silicone gums employed in the present invention may be terminated by triorganosilyl groups of the formula R'$_3$ where R' is a radical of monovalent hydrocarbons containing from 1 to 6 carbon atoms, hydroxyl groups, alkoxyl groups and mixtures thereof.

According to preferred embodiments, Component B/Layer B comprises at least one shine (gloss) enhancing agent.

According to preferred embodiments, Component B/Layer B has a self-leveling property which results in a flatter interface between Layer A and Layer B and/or between Layer B and air, and this flatter interface results in light diffraction, refraction and/or reflection properties for Layer B which enhances the shine of the composition.

According to preferred embodiments of the present invention, at least two silicone compounds such as silicone fluids (for example, phenylated silicones described above) and/or silicone gums are present in the compositions of the present invention.

According to preferred embodiments, if present, agent(s) which facilitate self-leveling of a layer such as silicone gum(s) is/are preferably present in an amount of from about 0.01% to about 90% by weight, preferably from 1% to 85% by weight, and preferably from 5% to 80% by weight of the total weight of the composition, including all ranges and subranges therebetween.

According to preferred embodiments, if present, agent(s) which have a high refractive index such as phenylated silicone oil(s) is/are preferably present in an amount of from about 0.05% to about 90% by weight, preferably from 0.1% to 75% by weight, and preferably from 1% to 50% by weight of the total weight of the composition, including all ranges and subranges therebetween.

According to preferred embodiments of the present invention, at least two silicone compounds such as silicone fluids (for example, phenylated silicones described above) and/or silicone gums are present in the compositions of the present invention.

According to preferred embodiments, the shine enhancing (s) is/are preferably present in an amount of from about 0.05% to about 90% by weight, preferably from 0.1% to 50% by weight, and preferably from 1% to 35% by weight of the total weight of the composition, including all ranges and subranges therebetween.

Matte Enhancing Agents (Mattifying Agent)

According to preferred embodiments of the present invention, at least one matte enhancing agent can be added to Component A, Component B, or both. With respect to Component B, the at least one matte enhancing agent can be added regardless of whether Component B is not self-leveling and/or Layer B has refractive properties to impart matte properties to the composition as described above.

Suitable matte enhancing agents include, but are not limited to, mattifying fillers such as, for example, talc, silica, silicone elastomers, and polyamides, and waxes such as, for example, beeswax and *Copernicia cerifera* (carnauba) wax.

According to preferred embodiments, the matte enhancing agent(s) is/are preferably present in an amount of from about 0.05% to about 90% by weight, preferably from 0.1% to 50% by weight, and preferably from 1% to 35% by weight of the total weight of the composition, including all ranges and subranges therebetween.

Coloring Agents

According to one or more embodiments of the present invention, compositions further comprising at least one coloring agent are provided. Preferably, such colored compositions can be cosmetic compositions such as, for example, foundations or eye shadows. According to such embodiments, the at least one coloring agent may be chosen from pigments, dyes, nacreous pigments, and pearling agents.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

If present, the coloring agents may be present in the composition in a concentration ranging up to 50% by weight of the total weight of the composition, such as from 0.01% to 40%, and further such as from 0.1% to 30%, including all ranges and subranges therebetween. In the case of certain products, the pigments, including nacreous pigments, may, for example, represent up to 50% by weight of the composition.

Embodiments without coloring agents (e.g., an inorganic or organic pigment or pearl zing agents) or with relatively low amounts of coloring agents may be suitable as primers for the skin. As used herein, a "primer" or "undercoat" is a preparatory coating put on keratinous materials (e.g., the skin or lips), before the application of subsequent cosmetic product layers. Priming can allow for better adhesion of these subsequent layers to the surface and increase their durability. For example, priming the skin or other keratinous material can also provide additional protection for the material especially in terms of extending the wear. Priming the skin or other keratinous material can also help to preserve the integrity of the subsequent cosmetic layers from fading, creasing, continued color intensity throughout the wear, particularly those comprising the compositions disclosed herein. Additionally, the primer can provide a uniform undercoat oftentimes resulting in increased uniformity of the color and texture of the following coat(s). Thus, such primers may act as a base for another foundation or eye shadow composition, for example, which may increase smoothness or help the other composition to better adhere. Such primers may also comprise mattifying agents or elastomers (e.g., silicone elastomers).

Alternatively, embodiments without coloring agents (e.g., an inorganic or organic pigment or pearlizing agents) or with relatively low amounts of coloring agents may be suitable as topcoats, such as compositions for application to lip compositions or foundations. As used herein, a "topcoat" is a coating put on prior cosmetic product layers after the application of the cosmetic products to keratinous materials (e.g., lips or skin).

Alternatively, embodiments without coloring agents (e.g., an inorganic or organic pigment or pearlizing agents) or with relatively low amounts of coloring agents may be stand-alone products, neither topcoats or primers, for application to keratinous materials.

According to the preceding embodiment, the compositions of the present invention contain less than 1% of coloring agents.

According to the preceding embodiment, the compositions of the present invention contain less than 0.5% of coloring agents.

According to the preceding embodiment, the compositions of the present invention contain no coloring agent.

Compositions of the present invention may further comprise at least one fatty substance. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexadecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

In one or more embodiments, a cosmetic composition of the present invention may also contains at least one high viscosity ester. Examples thereof include, but not limited to, $C_1$-$C_{30}$ monoesters and polyesters of sugars and related materials. These esters are derived from a sugar or polyol moiety and one or more carboxylic acid moieties. Depending on the constituent acid and sugar, these esters can be in either liquid or solid form at room temperature. Suitable liquid esters include, but are not limited to: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Suitable solid esters may include, but are not limited to: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. In an embodiment, the ester is a sucrose polyester in which the degree of esterification is 7-8, and in which the fatty acid moieties are C18 mono- and/or di-unsaturated and behenic, in a molar ratio of unsaturates:behenic of 1:7 to 3:5. In another embodiment, the sugar polyester is the octaester of sucrose in which there are about 7 behenic fatty acid moieties and about oleic acid moiety in the molecule. Other materials may include cottonseed oil or soybean oil fatty acid esters of sucrose.

In one or more embodiments, the high viscosity ester comprises sucrose acetate isobutyrate. One example of a suitable sucrose acetate isobutyrate compound is SAIB-100®, commercially available from Eastman®, Kingsport, Tenn. This ester has a viscosity of about 100,000 cps at 30° C. and a refractive index of about 1.5 at 20° C.

Acrylic Polymers

According to preferred embodiments, if present, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to preferred embodiments of the present invention, the compositions of the present invention further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to particularly preferred embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

According to preferred embodiments of the present invention, the compositions of the present invention further include at least one long-chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

According to preferred embodiments, the compositions of the present invention contain less than 1% wax.

According to preferred embodiments, the compositions of the present invention contain less than 0.5% wax.

According to preferred embodiments, the compositions of the present invention contain no wax.

If present, the wax or waxes may be present in an amount ranging from 1 to 30% by weight relative to the total weight of the composition, for example from 2 to 20%, and for example from 3 to 10%, including all ranges and subranges therebetween.

Additional Additives

According to preferred embodiments, the compositions of the present invention are compositions for application to keratinous material such as skin or lips. In accordance with these embodiments, the compositions of the present invention can contain ingredients typically found in cosmetic compositions such as, for example, water, active ingredients, humectants, surfactants and fillers. The composition of the invention can thus comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

In one or more embodiments, the composition of the invention is cosmetically or dermatologically acceptable, i.e., it should contain a non-toxic physiologically acceptable medium and should be able to be applied to the skin of human beings.

In particular, suitable gelling agents for the oil phase include, but are not limited to, lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminum, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminum silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R9720" "AEROSIL R974®" by the company Degussa, "CAB-O-SIL TS-610®", "CAB-O-SIL TS-720®" by the company Cabot.

Suitable emollients may include, but are not limited to, the following: natural and synthetic oils such as mineral, plant and animal oils; fats and waxes; fatty alcohols and acids, and their esters; esters and ethers of (poly)alkylene glycols; hydrocarbons such as petrolatum and squalane; lanolin alcohol and its derivatives; animal and plant triglycerides; and stearyl alcohol. Non-limiting examples include, without limitation, esters such as isopropyl palmitate, isopropyl myristate, isononyl isononanoate (such as WICKENOL 151 available from Alzo Inc. of Sayreville, N.J.), C12-C15 alkyl benzoates (such as FINSOLV TN from Innospec Active Chemicals), caprylic/capric triglycerides, pentaerythritol tetraoctanoate, mineral oil, dipropylene glycol dibenzoate, PPG-15 stearyl ether benzoate, PPG-2-Myristyl Ether Propionate, ethyl methicone, diethylhexylcyclohexane, hydrocarbon-based oils of plant origin, such as liquid triglycerides of fatty acids containing from 4 to 10 carbon atoms, for instance heptanoic or octanoic acid triglycerides, sunflower oil, corn oil, soybean oil, marrow oil, grapeseed oil, sesame seed oil, hazelnut oil, apricot oil, macadamia oil, arara oil, coriander oil, castor oil, avocado oil, jojoba oil, shea butter oil, caprylyl glycol; synthetic esters and ethers, especially of fatty acids, for instance, Purcellin oil, 2-octyldodecyl stearate, 2-octyldodecyl erucate, isostearyl isostearate, hydroxylated esters, for instance isostearyl lactate, octyl hydroxystearate, octyldodecyl hydroxystearate, diisostearyl malate or triisocetyl citrate, fatty alcohol heptanoates, octanoates or decanoates, polyol esters, for instance propylene glycol dioctanoate, neopentyl glycol diheptanoate and diethylene glycol diisononanoate, pentaerythritol esters, for instance pentaerythrityl tetraisostearate, isopropyl lauroyl sarcosinate, petroleum jelly, polydecenes, hydrogenated polyisobutene such as Parleam oil, and/or the mixture of n-undecane and of n-tridecane sold under the reference Cetiol UT by the company BASF.

Preferably, the emollient agent(s), if present, is present in the composition of the present invention in amounts of active material generally ranging from about 0.1% to about 20%, preferably from about 0.25% to about 15%, and more preferably from about 0.5% to about 10%, by weight, based on the total weight of the composition, including all ranges and subranges in between.

Suitable preservatives for skin compositions include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylchloroisothiazolinone, methylisothiazolinone, and any combination thereof. The heat-protective composition generally contains from about 0.001% to about 20% by weight of preservatives, based on 100% weight of total heat-protective composition. In another aspect, the composition contains from about 0.1% to about 10% by weight of preservatives, based on 100% weight of total heat-protective composition.

The compositions may also optionally comprise UV filters. UV filters are well known in the art for their use in stopping UV radiation. For example, the UV filter may be one or more organic UV filters and/or one or more inorganic UV filters. Non-limiting examples of UV filters include:

i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.

ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);

iii. Inorganic UV filters such as titanium oxide and zinc oxide, iron oxide, zirconium oxide and cerium oxide; and iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranilic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Suitable UV filters can include broad-spectrum UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl salicylate, octocrylene, polysilicone-15, butyl methoxydibenzoylmethane, menthyl anthranilate, and ethylhexyl dimethyl PABA.

Furthermore, combinations of UV filters may be used. For example, the combination of UV filters may be octocrylene, avobenzone (butyl methoxydibenzoylmethane), oxybenzone (benzophenone-3), octisalate (ethylhexyl salicylate), and homosalate, as described in U.S. Pat. No. 9,107,843, which is incorporated herein by reference in its entirety.

Methods

According to preferred embodiments of the present invention, methods of treating, caring for and/or making up keratinous material, such as skin or lips, by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

According to preferred embodiments of the present invention, methods of applying compositions of the present invention to a keratinous material (for example, skin or lips) comprising mixing or blending the composition so that the immiscible components are temporarily miscible, and applying the composition comprising the temporarily miscible components to the keratinous material are provided. In one or more embodiments, composition may be mixed in a mixing pack or may be mixed by hand. Subsequent to application to the keratinous material, the components separate to form a multilayer structure on the keratinous material.

According to preferred embodiments of the present invention, kits comprising (1) at least one container; (2) at least one applicator; and (3) at least one composition capable of forming a multilayer structure after application to a keratinous material, wherein the composition comprises at least two immiscible components prior to application.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Also in accordance with the preceding preferred embodiments, compositions are preferably contained in a suitable container for cosmetic compositions. Suitable shapes of such containers include, but are not limited to, any geometric shape such as, for example, square, rectangular, pyramidal, oval, circular, hemispherical, etc. Further, the container may be made of flexible or inflexible material.

Similarly, any applicator suitable for application of cosmetic compositions can be used in accordance with the present invention, with suitable examples of types of applicators including, but not limited to, a brush, stick, pad, roller ball, etc.

Preferably, either (1) the container is capable of mixing or blending the composition of the present invention so that the immiscible components are temporarily miscible; (2) the applicator is capable of mixing or blending the composition of the present invention so that the immiscible components are temporarily miscible; or (3) the container and the applicator working together are capable of mixing or blending the composition of the present invention so that the immiscible components are temporarily miscible in accordance with the preceding preferred embodiments. For example, a flexible container by virtue of its flexibility could create sufficient forces when manipulated to temporarily mix or blend the composition of the present invention so that the immiscible components are temporarily miscible; an applicator by virtue of its design could create sufficient forces when withdrawn from the container to temporarily mix or blend the composition of the present invention so that the immiscible components are temporarily miscible; or (3) an inflexible container and an applicator by virtue of their synergistic design elements could create sufficient forces when the applicator is withdrawn from the container to temporarily mix or blend the composition of the present invention so that the immiscible components are temporarily miscible.

According to preferred embodiments, the compositions of the present invention are lip compositions for application to lips such as lipsticks, lip gloss or lip balms. In accordance with these embodiments, the compositions of the present invention can contain ingredients typically found in lip compositions such as, for example, coloring agents, waxes, and gelling agents. Further, the compositions can contain water or be anhydrous. Also, the compositions can be solid or non-solid.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Compositions

Compositions falling with the specified ranges below were prepared and analyzed.

| Ingredient | Comparative A | Comparative B | Invention C | Invention D | Comparative E |
|---|---|---|---|---|---|
| Coloring Agent | 5-10 | 5-10 | 5-10 | 5-10 | 5-10 |
| Shine enhancing agent(s) | 5-10 | 5-10 | 5-10 | 5-10 | 5-10 |
| Thickening Agent(s) | 0.1-5 | 0.1-5 | 0.1-5 | 0.1-5 | 0.1-5 |
| Preservative(s) | 0.1-1.0 | 0.1-1.0 | 0.1-1.0 | 0.1-1.0 | 0.1-1.0 |
| Viscous Combination of Silicone Compounds | 18-24 | 18-24 | 18-24 | 18-24 | 18-24 |
| Trimethylsiloxysilicate and polypropylsilsesquioxane | 20-30 | 0 | 10-16 | 15-20 | 0 |
| Polymethylsilsesquioxane/trimethysiloxysilicate | 0 | 20-28 | 10-14 | 5-10 | 0 |
| Volatile Hydrocarbon | QS | QS | QS | QS | QS |

Of particular note, Inventive composition C had a (MQ resin+polypropylsilsesquioxane) to modified MQ resin weight ratio of 1:1, and Inventive composition D had a (MQ resin+polypropylsilsesquioxane) to modified MQ resin weight ratio of 2:1.

Comparative composition A did not contain modified MQ resin. Comparative composition B did not contain MQ resin+polypropylsilsesquioxane. Comparative composition E did not contain either modified MQ resin, MQ resin or polypropylsilsesquioxane.

Compositions A-D all contained the same amount of silicone resin by weight.

Example 2—Testing

The compositions from example 1 were tested for wear properties. Quantitative assessments were made with respect to the effect olive oil, artificial saliva and acetic acid had on wear properties as follows.

A 1 mL draw down on abrasion paper was prepared, and the film was permitted to sit at ambient temperature for 48 hours.

ASTM tape was used to traverse the right side of the film, with slight finger pressure across the film and at a 180 degree angle, and the film was gently removed.

On the film, droplets were placed on each sample. 4 droplets of olive oil (two top, two bottom) were used. This procedure (4 droplets total) was repeated for artificial saliva and acetic acid. The droplets were place to avoid overlap.

The droplets were allowed to sit for 10 min, and then wiped with cotton pads 15 times.

This testing was performed in duplicate. The following numerical rating system was used: a scale of 1-3 was assigned to results, where 1=least transfer/best film property and 3=most transfer/worst film property.

The results (reported as an average of the duplicate runs) are reported in the following table.

Each sample was analyzed for its longwearing properties on the film itself (how much of the film was rubbed away) as well as transfer of the film to the cotton pads used for wiping. In the above table, "cotton" refers to testing related to transfer to cotton pads.

Comparative composition A exhibited some disruption in the presence of olive oil as well as transfer to the ASTM tape. Comparative composition B exhibited an inferior wear profile with an average wear of 2 out of 3. This sample showed lower performance for olive oil, saliva, and acetic acid as well as transfer to the cotton pads as compared to comparative composition A. And it showed similar performance on the ASTM tape transfer to comparative composition A.

Invention composition C (1:1 ratio) surprisingly showed an excellent wear profile with an average wear of 1.22 out of 3. Interestingly, the oil disruption of the film in invention composition C was better than in comparative compositions A and B.

Invention composition D (2:1 ratio) showed a similar excellent wear profile to invention composition C, with an average wear of 1.21 out of 3 indicating that the combination of the silicone resins provided an improved wear profile.

We have shown that 1:1 and 2:1 ratios of (MQ resin+polypropylsilsesquioxane) to modified MQ resin in the invention compositions performed significantly better than either (MQ resin+polypropylsilsesquioxane) or modified MQ resin alone.

What is claimed is:

1. A cosmetic composition capable of forming a multi-layer structure after application to a keratinous material, wherein the cosmetic composition comprises at least two immiscible components A and B prior to application and wherein Component A and Component B are separated in the cosmetic composition prior to application: wherein component A comprises at least one MQ resin, at least one polypropylsilsesquioxane, and at least one modified MQ resin, wherein the at least one modified MQ resin is polymethylsilsesquioxane/trimethylsiloxysilicate and wherein the at least one MQ resin is trimethylsiloxysilicate; and wherein component B comprises about 0.01% to 90% by weight with respect to the total weight of the composition of one or more silicone compounds in an amount sufficient to achieve a

|  | Oil | Oil Cotton | Saliva | Saliva Cotton | Acetic Acid | A.A. Cotton | ASTM | Average Score |
|---|---|---|---|---|---|---|---|---|
| Comp A | 1.50 | 2.00 | 1.06 | 1.50 | 1.00 | 1.50 | 2.00 | 1.51 |
| Comp B | 2.50 | 2.00 | 1.75 | 1.50 | 1.75 | 2.50 | 2.00 | 2.00 |
| Inv C | 1.00 | 1.50 | 1.00 | 1.38 | 1.00 | 1.44 | 1.50 | 1.22 |
| Inv D | 1.00 | 1.50 | 1.00 | 1.25 | 1.00 | 1.50 | 1.88 | 1.21 |
| Comp E | 3.00 | 3.00 | 2.00 | 2.25 | 2.00 | 2.50 | 2.88 | 2.46 | viscosity of about 1,000 cSt to 22,000,000 cSt, and wherein, prior to application to keratinous material, the cosmetic composition is mixed such that Component A and Component B are temporarily miscible upon application to keratinous material and, after application to keratinous material, Component A separates from Component B to form a multilayer structure on keratinous material comprising Layer A corresponding to Component A and Layer B corresponding to Component B, wherein the at least one MQ resin, the at least one polypropylsilsesquioxane, and the at least one modified MQ resin are present in the composition in a weight ratio of (1) the at least one MQ resin and the at least one polypropylsilsesquioxane to (2) the at least one modified MQ resin from about 2:1 to about 1:3.

2. The cosmetic composition of claim 1, further comprising at least one colorant.

3. The cosmetic composition of claim 2, wherein the at least one colorant is an inorganic pigment.

4. The cosmetic composition of claim 2, wherein the composition comprises less than 1% of the at least one colorant by weight with respect to the total weight of the composition.

5. The cosmetic composition of claim 1, further comprising at least one volatile hydrocarbon oil.

6. The cosmetic composition of claim 5, wherein the at least one volatile hydrocarbon oil is isododecane.

7. The cosmetic composition of claim 1, wherein the one or more silicone compounds comprises at least one compound selected from the group consisting of a silicone gum, a silicone fluid, and mixtures thereof.

8. A kit comprising: (a) the cosmetic composition of claim 1; (b) at least one container which contains the cosmetic composition; and (c) at least one applicator.

9. The kit of claim 8, wherein the at least one container is configured to mix Components A and B.

10. The cosmetic composition of claim 1, wherein the weight ratio of (1) the at least one MQ resin and the at least one polypropylsilsesquioxane to (2) the at least one modified MQ resin is from about 2:1 to about 1:2.

11. The cosmetic composition of claim 1, wherein the weight ratio of (1) the at least one MQ resin and the at least one polypropylsilsesquioxane to (2) the at least one modified MQ resin is from about 1:1 to about 1:2.

12. The cosmetic composition of claim 1, wherein the weight ratio of (1) the at least one MQ resin and the at least one polypropylsilsesquioxane to (2) the at least one modified MQ resin is from about 1:1 to about 2:1.

13. A method of applying the cosmetic composition of claim 1 to a keratinous material comprising mixing the cosmetic composition to form a mixed composition in which Component A and Component B are temporarily miscible, and applying the mixed composition to the keratinous material.

* * * * *